United States Patent

Behnam et al.

Patent Number: 6,048,566
Date of Patent: Apr. 11, 2000

[54] NON-ALCOHOLIC BEVERAGE AND PROCESS OF MAKING

[75] Inventors: Dariush Behnam, Rossdorf; Erich F. Elstner, Grobenzell; Michael Wannenmacher, Heidelberg, all of Germany

[73] Assignee: Aquanova Getranketechnologie GmbH, Mannheim, Germany

[21] Appl. No.: 09/101,023

[22] PCT Filed: Nov. 14, 1997

[86] PCT No.: PCT/EP97/06360

§ 371 Date: Jun. 29, 1998

§ 102(e) Date: Jun. 29, 1998

[87] PCT Pub. No.: WO98/21984

PCT Pub. Date: May 28, 1998

[30] Foreign Application Priority Data

Nov. 15, 1996 [DE] Germany .......................... 196 47 352

[51] Int. Cl.[7] ........................................................ A23L 2/52
[52] U.S. Cl. ............................... 426/590; 426/66; 426/67; 426/72; 426/74; 426/590; 426/599; 424/439
[58] Field of Search ................................. 426/590, 74, 66, 426/67, 599, 72; 424/439

[56] References Cited

U.S. PATENT DOCUMENTS

| | | | |
|---|---|---|---|
| 4,743,449 | 5/1988 | Yoshida et al. | 424/420 |
| 4,751,241 | 6/1988 | Motoyama et al. | 514/532 |
| 5,626,849 | 5/1997 | Hastings et al. | 424/195.1 |
| 5,814,222 | 9/1988 | Zelenák et al. | 426/67 |
| 5,817,351 | 10/1998 | DeWille et al. | 426/74 |

*Primary Examiner*—Helen Pratt
*Attorney, Agent, or Firm*—Jacobson, Price, Holman & Stern, PLLC

[57] ABSTRACT

A nonalcoholic beverage such as table water, mineral water or the like is described. In order to develop a well-tolerated composition which can be administered easily and which permits the body to be supplied almost incidentally with a desirable dose of ubiquinone Q 10, it is provided that it comprises 10 mg/l to 500 mg/l of ubiquinone Q 10. A production process envisages dissolving ubiquinone Q 10 in a solubilizer, and adding the solution to the beverage.

22 Claims, No Drawings

NON-ALCOHOLIC BEVERAGE AND PROCESS OF MAKING

Mitochondrial electron transport in the respiratory chain is composed of various components, one of which is coenzyme Q (ubiquinone). Ubiquinone has an interesting function because it forms a transition between a 2-electron transport, originating from the electron donor NADH or succinate, into a 1-electron transport of the cytochrome chain. This function of ubiquinone has been known for a long time. The ubiquinone point in mitochondrial electron transport is a switching point. Electrons reach ubiquinone from various donors and reduce it to hydroquinone which in turn releases electrons again to the cytochrome chain. There is moreover alternation of 1- and 2-electron transitions so that a hydroquinone-semiquinone-quinone cycle is superimposed. Through this electron transition, not only reducing equivalents but also protons pass through the mitochondrial membrane, which results in a proton gradient which is in turn utilized for ATP synthesis.

Thus, ubiquinone is very considerably involved in the conversion of the energy present in the diet into the body's own energy (ATP). CoQ10 is therefore often referred to as energy activator.

It has been possible to show in various sports medical investigations using CoQ10 in competitive sportspersons that there is a correlation between increased performance and elevated CoQ10 plasma level.

The causes of an inadequate supply of CoQ10 are:
a) Reduced Q10 synthesis:

It is known that there is a great reduction in the Q10 concentration in the tissues of various organs, especially in the heart, with increasing age.

The decrease in the CoQ10 level is greater than the age-related fall in other lipids in the human body.
b) Increased CoQ10 requirement:

With great physical exercise such as, for example, sports, heavy work or with stress, the body requires correspondingly larger amounts of CoQ10. The reason for this is the increased energy turnover which makes greater demands on the electron transport system, which means that increased amounts of ubiquinone CoQ10 are required. In exercise situations, as in sports, the CoQ10 level in the plasma is reduced.
c) Reduced alimentary intake:

Although CoQ10 is present in various foodstuffs such as fish, meat, soybeans, corn and nuts, its temperature sensitivity means that it is often almost completely destroyed during boiling or roasting.

A serious decline in ubiquinone can be measured in various pathological states. However, this decline relates not only to the ubiquinone found in the mitochondria but also in particular to the ubiquinone which is present in the cytoplasm or bound to other organelles. On the other hand, however, there is evidence that sports training (physical exercise) not only increases the level of the usual antioxidants but also stimulates ubiquino [sic] synthesis. This fact itself indicates that ubiquinone has a function additional to that of an electron transport metabolite in intermediary metabolism: that of an antioxidative function in the sense of protecting from reactive oxygen species.

As has been mentioned, ubiquinone is found not only in the mitochondrial respiratory chain but also in all cellular membranes and in blood serum as well as in serum lipoproteins (especially in the LDL.) (Ernster and Dallner, 1995). It is thus not surprising that Kontush et al found that ubiquinone Q 10 acts as an efficient factor protecting against the oxidation of LDL by copper ions (Kontush et al. 1995). Several authors have reported that it is in particular the reduced coenzyme Q which performs this protective function. It is thus not surprising that coenzyme Q is reduced by membrane-bound NADPH or NADH reductases (DT diaphorases) (Takahashi et al. 1995; Beyer et al. 1996). In the reduced form, coenzyme Q protects in particular mitochondrial membranes from oxidative processes induced by adriamycin (a chemotherapeutic agent) (Beyer et al. 1996). In this protective function, coenzyme Q appears to act cooperatively with other antioxidants, especially with vitamin E and selenoperoxidase (gluthatione peroxidase) (Chen and Tappel 1994). Thus, coenzyme Q and α-tocopherol appear to act cooperatively in the complete pecking order of antioxidants (Noack et al. 1994, Beyer 1994). An interaction with hemoproteins has also been shown, and recycling of the ferryl status of hemoproteins by coenzyme Q might represent a novel antioxidative mechanism (Mordente et al. 1994).

In addition, Q 10 has also been assumed to have an immunomodulatory effect such that a deficiency of Q 10 in the myocardium leads to inflammatory reactions which can be improved by Q 10 doses (Folkers and Wolaniuk 1985).

Effects on the ischemic heart or on overstressed myocardium have been described most frequently for coenzyme Q, a stimulation of cardiac function having been observed (Hano et al. 1994, Chrestanello et al. 1996; Morita et al. 1995).

As is evident from numerous publications, the effects on the myocardial energy supply through ubiquinone 10 doses are documented best, and therapy with 100 mg a day has been regarded as very helpful in the therapies of various heart diseases (Mortensen 1993). Moreover other organs such as, for example, perfused rat liver (Genova et al. 1994), or excessive alcohol metabolism (Loop et al. 1994), stability of preserved lungs (Hanagiri et al. 1994), periodontal problems in connection with poor hygiene (Wilkinson et al. 1976), bypass operations (Morita 1995) and supplementary functions in the regulation of homocysteine-methionine metabolism in connection with deficiency status of vitamins B6, B12 and folic acid (Sinatra and DeMarco 1995) have, besides the protective function of the LDL, been described as extremely important.

The invention is based on the object of developing a well-tolerated composition which can be administered easily and which permits the body to be supplied almost incidentally with a desirable dose of ubiquinone Q10.

Used for this purpose is a nonalcoholic beverage such as table water, mineral water or the like, which comprises 10 mg/l to 500 mg/l of ubiquinone Q 10. Since the usual consumption of, for example, table water is generally widespread and relatively high, addition of Q 10 to a table water of this type simultaneously supplies the body with Q 10.

Q 10-containing beverages are in clear, turbidity-free form especially when the ubiquinone Q 10 is added as a solution, advantageously employing polyoxyethylene sorbitan monooleate (polysorbate 80, E 433) as solubilizer. After production, the beverage is packed into opaque containers which are, in particular, opaque to near and far ultraviolet light. It is also possible to use for this purpose containers, for example, cans which cover the entire spectrum of light Cans made of aluminum or aluminum alloys are preferably used. It is also possible to accommodate the beverage according to the invention in metal foil or aluminum foil sachets and in the Tetrapak which is known per se. Also suitable are certain plastics or natural materials such as rock and clay. If the material itself does not have the required property of opacity, it can be coated. There is also the possibility of using an opaque outer pack.

A process for producing a nonalcoholic beverage such as table water, mineral water or the like according to the invention comprises dissolving ubiquinone Q 10 in a solubilizer and adding the solution to the beverage. A suitable and preferred solubilizer is polyoxyethylene sorbitan monooleate (polysorbate 80, E433).

The efficacy of the beverage is extended if it is supplemented beyond its natural oxygen content with dissolved oxygen so that it expediently comprises an oxygen content of from 10 mg/l to 85 mg/l of dissolved oxygen. The sudden supply of oxygen to isolated bovine heart mitochondria which were incubated under hypoxic conditions results in lipid peroxidations both in the mitochondria and in submitochondrial particles, and oxidative damage to certain proteins. This damage can be alleviated by ubiquinone.

On the other hand, it was possible to show (M. J. Eble, F. Lohr, M. Wannenmacher in ONKOLOGIE, April 1995, page 136, and by M. J. Eble, B. Vanselow, A. Dietz, M. Wannenmacher in an investigation reported at the $2^{nd}$ German Congress on Radio-oncology, Radiobiology and Medical Physics in Baden-Baden on Nov. 16 to 19, 1996) that the increased oxygen content in a beverage, especially water, very greatly promotes blood flow in hypoxic tissue area by an as yet unknown facilitation effect. With this promotion, there may be, as well as on involvement in sports, a fall in the antioxidative potential in the short term, as has been shown for numerous ischemic and perfusion models. Prophylactic admixture of Q 10 and vitamin E in the beverage annuls these effects right from the outset.

It is particularly advantageous to add to the beverage selenium in a form which can be utilized by the body, for example, in a selenium concentration of 5 $\mu$g/l to 500 $\mu$g/l. Concerning this, the results of a prospective randomized double-blind study in the USA on 1312 patients suffering from nonmelanomatous skin cancers were presented at the $6^{th}$ International Selenium Symposium in Peking. It emerged from this that daily administration of 200 $\mu$g of selenium reduced the cancer mortality by 25%, the secondary cancer incidence by 52%, the lung cancer risk by 40%, the lung cancer mortality by 49%, the colorectal carcinoma incidence by 64%, the prostate carcinoma incidence by 59% and the bronchial carcinoma incidence by 40%.

The entire production and filling process expediently takes place with exclusion of light.

An example of the beverage according to the invention starts initially from the water from the Renata spring in D-64757 Rothenberg. Analysis carried out on May 24, 1995 thereon revealed values which are indicated in German Patent 195 29 955, columns 3 and 4. Express reference is made to these values here.

30 mg of ubiquinone Q 10 were dissolved in 105 mg of polyoxyethylene sorbitan monooleate (obtainable under the proprietary name Lamesorb SMO 20 from Grünau GmbH in D-89251 Illertissen, Postfach 10 63) heated to about 60° to give a clear, somewhat yellowish solution. This solution was added to 0.33 l of the abovementioned spring water and oxygenated. The oxygenation takes place in a manner described in detail in the International Patent Application with the publication number WO 95/32796. After the oxygen supplementation in the manner described therein, the oxygen ($O_2$) content was about 79 mg/l. This resulted in a clear beverage.

In another step, the contents of a 10 ml vial which contained 500 $\mu$g of selenium (obtainable under the proprietary name "selenase" from G.N. FARM Arzneimittel GmbH, Schorndorferstr. 32, D-70734 Fellbach) were added to the beverage. After the addition, an easily drinkable beverage which had retained its spring water characteristics was obtained.

If required, it is possible to add one or more fruit and/or vegetable juice concentrates and/or flavor improvers to the beverage.

In addition, the beverage is vitaminized with $B_1$ and/or $B_2$ and/or $B_3$ and/or vitamin E. Vitamin E eliminates possible derangements of the antioxidative potential with Q 10. Vitamin E is added as a solution to the beverage, employing for this solution the solubilizer already used for the ubiquinone Q 10. The beverage according to the invention acts to assist therapy both in neuro-degenerative disorders, depressive disturbances and in atherogenic processes (age, smoking).

In order to improve the taste of the beverage which can be used as dietary supplement, it can be flavored. Recommended for this is a mixture of about 1.38 g/l LIMETTE citrus, about 1.04 g/l cassis and about 1.04 g/l mango. It is further recommended to add about 20 g/l maltodextrin and about 50 g/l fructose. The finished beverage is expediently subjected to a primary and, where appropriate, a secondary filtration, in which case filters with a pore size of about 0.1$\mu$ to about 1.5$\mu$ have proven suitable. The beverage can then be used to fill containers which are opaque to light but at least opaque to ultraviolet, such as, for example, cans. The clear beverage has an excellent shelf life in the latter.

We claim:

1. Nonalcoholic clear beverage comprising from 10 to 500 mg/l of ubiquinone Q10 and a polysorbate solubilizer in a nonalcoholic clear liquid.

2. Beverage according to claim 1, further comprising selenium in a form which can be utilized by the body.

3. Beverage according to claim 2, wherein the selenium concentration is 5 to 500 $\mu$g/l.

4. Beverage according to claim 2, wherein the beverage is flavored.

5. Beverage according to claim 4, wherein the beverage is flavored with one or more fruit juice concentrates or flavor improvers or mixtures thereof.

6. Beverage according to claim 5, wherein the beverage is flavored with about 1.04 g/l cassis and about 1.04 g/l mango.

7. Beverage according to claim 1, further comprising about 20 g/l maltodextrin and about 50 g/l fructose.

8. Beverage according to claim 1, wherein ubiquinone Q10 is in solution in water.

9. Beverage according to claim 1, further comprising vitamin E.

10. Beverage according to claim 9, wherein the vitamin E is in solution in water.

11. Beverage according to claim 1, wherein the beverage is in an opaque container identifying a daily recommended dose.

12. Beverage according to claim 11, wherein the container is opaque to near and far ultraviolet light.

13. Liquid base for preparing a beverage according to claim 1 which contains ubiquinone Q10 dissolved in a nonalcoholic clear liquid by a solubilizer.

14. Liquid base according to claim 13 wherein the solubilizer is polyoxyethylene sorbitan monooleate.

15. Nonalcoholic clear beverage comprising from 10 to 500 mg/l of ubiquinone Q10 and polyoxyethylene sorbitan monooleate as a solubilizer in a nonalcoholic clear liquid.

16. Nonalcoholic clear beverage according to claim 15, wherein the beverage contains approximately 300 mg/l of the polyoxyethylene sorbitan monooleate.

17. Process for the production of a nonalcoholic clear beverage comprising dissolving ubiquinone Q10 in a nonalcoholic clear liquid with a polysorbate solubilizer, and adding the solution to the beverage.

18. Process according to claim 17, wherein the solubilizer is polyoxyethylene sorbitan monooleate.

19. Process according to claim 17, further comprising adding selenium to the beverage in a form which can be utilized by the body.

20. Process according to claim 17, further comprising adding vitamin E to the beverage.

21. Process according to claim 20, wherein the vitamin E is dissolved in a nonalcoholic clear liquid by a solubilizer, and the solution is added to the beverage.

22. Process according to claim 20, wherein polyoxyethylene sorbitan monooleate is the solubilizer for the vitamin E.

* * * * *